(12) United States Patent
Katsuragawa et al.

(10) Patent No.: US 9,072,807 B2
(45) Date of Patent: Jul. 7, 2015

(54) ABSORBENT ARTICLE HAVING PAD CONFIGURATION

(75) Inventors: Kunihiko Katsuragawa, Kanonji (JP); Kenichi Sasayama, Kanonji (JP); Makoto Ichikawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 110 days.

(21) Appl. No.: 13/882,365

(22) PCT Filed: Dec. 19, 2011

(86) PCT No.: PCT/JP2011/079288
§ 371 (c)(1),
(2), (4) Date: Apr. 29, 2013

(87) PCT Pub. No.: WO2012/101934
PCT Pub. Date: Aug. 2, 2012

(65) Prior Publication Data
US 2013/0218115 A1    Aug. 22, 2013

(30) Foreign Application Priority Data
Jan. 27, 2011    (JP) ................. 2011-015803

(51) Int. Cl.
*A61F 13/535*  (2006.01)
*A61L 15/58*  (2006.01)
*A61F 13/15*  (2006.01)
*A61F 13/47*  (2006.01)
*A61F 13/532*  (2006.01)
*A61L 15/22*  (2006.01)

(52) U.S. Cl.
CPC ........... *A61L 15/58* (2013.01); *A61F 13/15658* (2013.01); *A61F 13/47* (2013.01); *A61F 13/5323* (2013.01); *A61L 15/22* (2013.01)

(58) Field of Classification Search
CPC ................ A61F 13/5323; A61F 2013/530562; A61F 2013/530598; A61F 2013/5307; A61F 2013/53051; A61F 2013/530547
See application file for complete search history.

(56) References Cited

U.S. PATENT DOCUMENTS

| RE32,957 | E | * | 6/1989 | Elias et al. ..................... 604/368 |
| 4,935,021 | A | * | 6/1990 | Huffman et al. .......... 604/385.26 |
| 5,149,335 | A | * | 9/1992 | Kellenberger et al. ......... 604/372 |
| 5,411,497 | A | * | 5/1995 | Tanzer et al. .................. 604/368 |
| 5,601,542 | A | * | 2/1997 | Melius et al. .................. 604/368 |
| 5,800,419 | A | * | 9/1998 | Soga et al. ..................... 604/368 |
| 5,938,650 | A | * | 8/1999 | Baer et al. ..................... 604/368 |

(Continued)

FOREIGN PATENT DOCUMENTS

| JP | 05038350 A | 2/1993 |
| JP | 3732320 B2 | 1/2006 |

(Continued)

*Primary Examiner* — Susan Su
(74) *Attorney, Agent, or Firm* — Lowe Hauptman & Ham, LLP (57) ABSTRACT

An absorbent article having a pad configuration, including superabsorbent polymer particles. Superabsorbent polymer particles are interposed between opposed surfaces of first and second layers overlapping with each other to form an absorbent article. The article includes an absorbing region and a sealing region. In the absorbing region, the superabsorbent polymer particles are bonded to the second layer with a hot melt adhesive. In the sealing region, the first layer and the second layer are joined to each other to surround the absorbing region.

12 Claims, 4 Drawing Sheets

(56) References Cited

U.S. PATENT DOCUMENTS

| | | | |
|---|---|---|---|
| 6,610,900 B1* | 8/2003 | Tanzer | 604/368 |
| 8,524,355 B2* | 9/2013 | Nakaoka | 428/198 |
| 2002/0115969 A1* | 8/2002 | Maeda et al. | 604/368 |
| 2006/0184146 A1* | 8/2006 | Suzuki | 604/358 |
| 2007/0093164 A1* | 4/2007 | Nakaoka | 442/385 |
| 2007/0135784 A1* | 6/2007 | Tankersley | 604/357 |
| 2007/0156107 A1* | 7/2007 | Kimura et al. | 604/368 |
| 2007/0197987 A1* | 8/2007 | Tsang et al. | 604/365 |
| 2011/0313384 A1* | 12/2011 | Akiyama | 604/378 |
| 2012/0308799 A1* | 12/2012 | Yamaguchi et al. | 428/220 |
| 2012/0323195 A1* | 12/2012 | Ehrnsperger et al. | 604/366 |
| 2012/0328862 A1* | 12/2012 | Fukudome et al. | 428/220 |
| 2013/0018348 A1* | 1/2013 | Carlucci et al. | 604/372 |
| 2013/0110067 A1* | 5/2013 | Carlucci | 604/370 |
| 2013/0226120 A1* | 8/2013 | Van De Maele | 604/372 |
| 2014/0005625 A1* | 1/2014 | Wirtz et al. | 604/372 |
| 2014/0378926 A1* | 12/2014 | Ota et al. | 604/367 |

FOREIGN PATENT DOCUMENTS

| | | |
|---|---|---|
| JP | 2009131510 A | 6/2009 |
| JP | 2010063815 A | 3/2010 |
| JP | 2010273972 A | 12/2010 |
| WO | 2010082373 A1 | 7/2010 |
| WO | 2010113919 A1 | 10/2010 |

* cited by examiner

ABSORBENT ARTICLE HAVING PAD CONFIGURATION

RELATED APPLICATIONS

The present application is a National Phase of PCT/JP2011/079288, filed Dec. 19, 2011, and is based on, and claims priority from, Japanese Application Number 2011-015803, filed Jan. 27, 2011.

TECHNICAL FIELD

The present invention relates to absorbent articles having a pad configuration and more particularly to absorbent articles having a pad configuration suitable to be used as absorbent structures in absorbent wearing articles, for example, disposable diapers, or to be used, for example, as disposable wipes.

BACKGROUND

Absorbent pads including superabsorbent polymer particles interposed between two sheet materials of which at least one is water-permeable is widely known.

For example, the absorbent sheet disclosed in JP H5-38350 A (PTL 1) as an example of the absorbent articles is produced by following the steps of coating a sheet-like absorptive material with adhesive, dispersing superabsorbent polymer particles thereover, overlapping another sheet-like absorptive material therewith and finally integrating them under compression.

In the disposable wearing article disclosed in JP 3732320 B2 (PTL 2), a plurality of tubular portions extending in parallel to each other are formed of a water-permeable intermediate sheet underlying a liquid-permeable upper sheet and liquid-impermeable lower sheet wherein these tubular portions contain liquid-absorbent material including superabsorbent polymer particles in a range of 5 to 98% by mass.

In addition, the absorbent sheet disclosed in JP 2009-131510 A (PTL 3) is composed of an upper sheet, a lower sheet and superabsorbent polymer particles contained between these two sheets wherein the upper sheet and the lower sheet are partially joined to each other so as to surround respective non-bonded regions and to define respective pockets adapted to contain the superabsorbent polymer particles. Within the respective pockets, the superabsorbent polymer particles are movable.

CITATION LIST

Patent Literature

{PTL 1}: JP H5-38350 A
{PTL 2}: JP 3732320 B2
{PTL 3}: JP 2009-131510 A

SUMMARY

Technical Problem

The absorbent sheet disclosed in PTL 1 is composed of two sheet-like absorbent materials and superabsorbent polymer particles interposed between these two absorbent materials integrally joined with an adhesive. Consequently, the flexibility of the absorbent sheet as a whole might be lower than that of the respective absorbent materials.

In the liquid-absorbent article and the absorbent sheet disclosed in PTL 2 and PTL 3, respectively, the superabsorbent polymer particles movable at relatively high degree of freedom prior to water absorption and when these liquid-absorbent article and absorbent sheet are used in, for example, a disposable diaper, body exudates such as urine is unlikely to be efficiently absorbed depending on a posture of the diaper wearer.

An object of the present invention is to provide an absorbent article improved so as to solve such problems.

Solution to Problem

The present invention relates to an absorbent article having a pad configuration, including a first layer, a second layer, superabsorbent polymer particles interposed between the first and second layers of which at least one is water-permeable.

In the absorbent article, the present invention further includes the following features:

at least one of opposed surfaces of the first and second layers is formed with absorbing regions coated with a hot melt adhesive for fixation of the superabsorbent polymer particles and a sealing region coated with a hot melt adhesive for sealing and surrounding the absorbing regions;

each of the absorbing regions defines an existence region in which a required mass per unit area of the superabsorbent polymer particles bonded to the at least one of the opposed surfaces of the first and second layers with the hot melt adhesive for fixation of the superabsorbent polymer particles exists.

the sealing region defines a non-existence region in which the opposed surfaces of the first and second layers are joined to each other with the hot melt adhesive for sealing and an amount of the superabsorbent polymer particles corresponding to the required mass per unit area of the superabsorbent polymer particles in the absorbing region does not exist.

As used herein, by "non-existence region in which an amount of the superabsorbent polymer particles corresponding to a required mass per unit area does not exist" is meant that substantially none of the superabsorbent polymer particles exists in the sealing region or, if exists, the required mass per unit area in the sealing region is smaller than the required mass per unit area in the absorbing region and the sealing region fulfills its function.

According to an embodiment of the present invention, in the existence region in which the required mass per unit area of the superabsorbent polymer particles exists, the superabsorbent polymer particles are fixed thereto with a mass per unit area in a range of 30 to 300 $g/m^2$.

According to another embodiment of the present invention, an amount of the hot melt adhesive for sealing applied to the at least one of the opposed surfaces of the first and second layers per unit area is equal to or larger than an amount of the hot melt adhesive for fixation of the superabsorbent polymer particles applied to the at least one of the opposed surfaces of the first and second layers per unit area.

According to even another embodiment of the present invention, a plurality of the absorbing regions is formed.

According to still another embodiment of the present invention, the first and second layers are water-permeable.

According to yet another embodiment of the present invention, the first and second layers being water-permeable are formed of hydrophilic nonwoven fabrics of thermoplastic synthetic fibers.

According to further another embodiment of the present invention, one of the first and second layers is formed of a water-permeable sheet and a remainder of the first and second layers is formed of a water-impermeable or low-water-permeable sheet and the superabsorbent polymer particles are bonded to the water-impermeable or low-water-permeable sheet.

According to an alternative embodiment of the present invention, the water-impermeable or low-water-permeable sheet is a hydrophobic nonwoven fabric of thermoplastic synthetic fibers or a laminate composed of the nonwoven fabric and a water-impermeable plastic film, and the superabsorbent polymer particles are bonded to the hydrophobic nonwoven fabric.

According to another alternative embodiment of the present invention, wherein the hot melt adhesive for fixation of the superabsorbent polymer particles in the absorbing regions and the hot melt adhesive for sealing in the sealing region are applied so as to be continuous to one another or so as to be adjacent to one another.

According to even another alternative embodiment of the present invention, the superabsorbent polymer particles have a water-absorption speed $AS_1$ and, between the opposed surfaces of the first and second layers, second superabsorbent polymer particles having a water-absorption speed $AS_2$ lower than the water-absorption speed $AS_1$ are included between the opposed surfaces of the first and second layers defining the absorbing regions.

According to still another alternative embodiment of the present invention, the second superabsorbent polymer particles are bonded to a remainder of the opposed surfaces of the first and second layers with a second hot melt adhesive for fixation of the superabsorbent polymer particles.

According to yet another alternative embodiment of the present invention, the second superabsorbent polymer particles are movable between the opposed surfaces of the first and second layers.

According to further another alternative embodiment of the present invention, the hot melt adhesive for fixation of the superabsorbent polymer particles and the hot melt adhesive for sealing are the same adhesive.

As used herein, by "the opposed surface the first and second layers is coated with a hot melt adhesive" is meant that, without regard to the types of the hot melt adhesive, one of the opposed surfaces of the first and second layers is joined to the hot melt adhesive. In other words, the one of the opposed surfaces of the first and second layers is directly coated with the hot melt adhesive or this one of the opposed surfaces of the first and second layers comes in contact with the hot melt adhesive applied to the other of the opposed surfaces of the first and second layers and, in consequence, the one of the opposed surfaces of the first and second layers is joined to the other of the opposed surfaces of the first and second layers.

Advantageous Effects of Invention

In the absorbent article according to the present invention, the first and second layers overlapping each other are joined together in the sealing region but, in the absorbing region, the superabsorbent polymer particles are interposed and prevent these layers from being joined together. In this way, the flexibility of the absorbent article should not be deteriorated due to integrally joining of these layers. In addition, the superabsorbent polymer particles fixed to one of the opposed surfaces of the first and second layers in the absorbing regions should not be unevenly distributed irrespective of postures assumed by the wearer of the absorbent article.

DESCRIPTION OF EMBODIMENTS

An absorbent article having a pad configuration according to the present invention will be described in detail hereunder with reference to the accompanying drawings.

Figure 1:
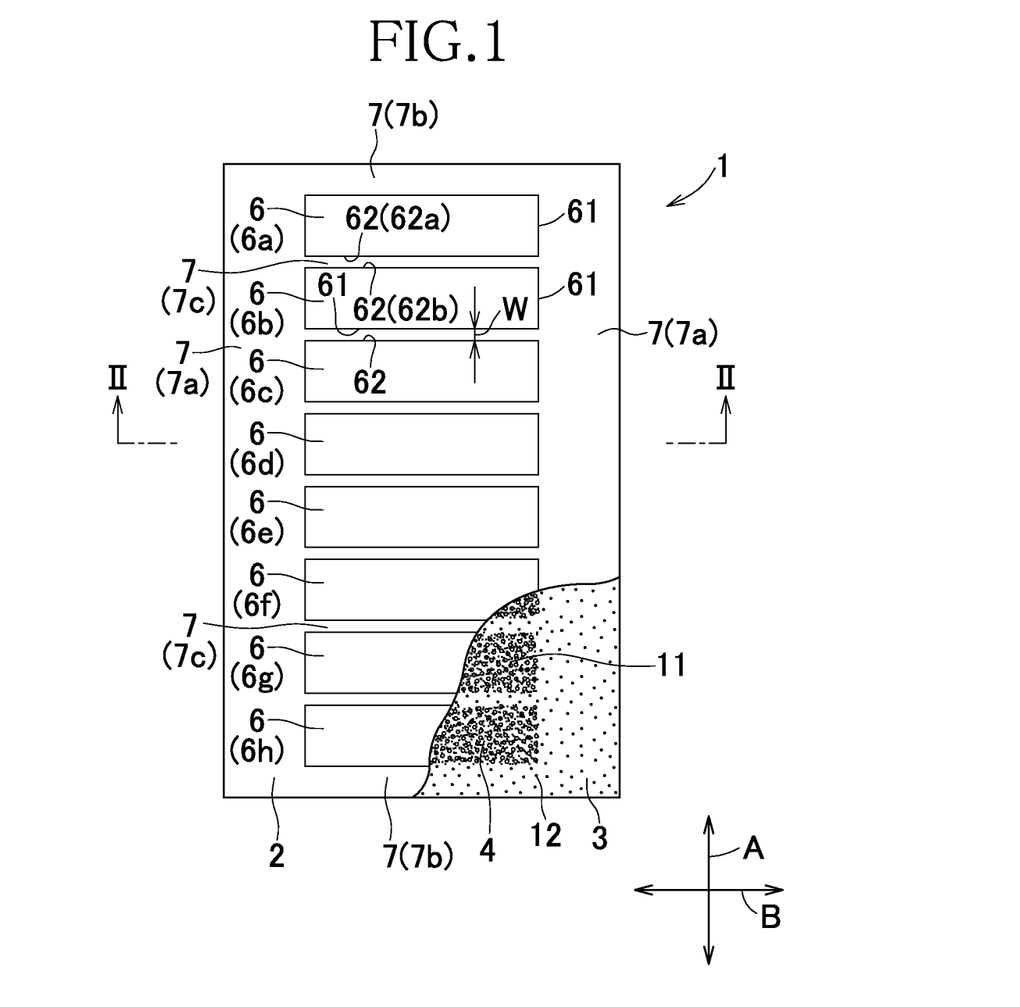
FIG. 1 is a partially cutaway plan view of an absorbent article.
Figure 2:
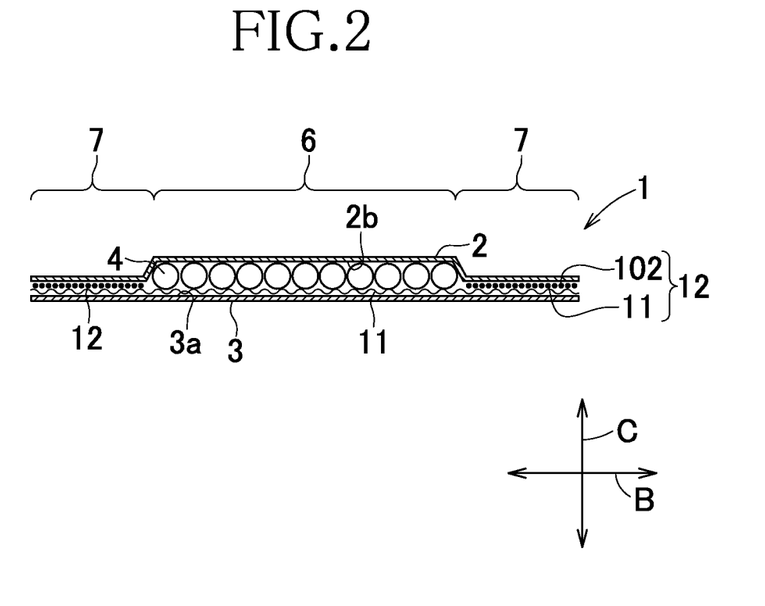
FIG. 2 is a sectional view taken along line II-II in FIG. 1.

FIG. 1 is a partially cutaway plan view of an absorbent article 1 having a pad configuration and FIG. 2 is a sectional view taken along line II-II in FIG. 1 wherein double-headed arrows A, B and C respectively indicate a longitudinal direction, a transverse direction and a thickness direction which are orthogonal to each other. Referring to FIGS. 1 and 2, the article 1 includes a water-permeable upper layer 2, a water-permeable or low-water-permeable or water-impermeable lower layer 3 and superabsorbent polymer particles 4. While various kinds of polymers well known to those skilled in the art are available for the superabsorbent polymer particles, for example, sodium polyacrylate-based polymers which are water-insoluble and have a water-absorbing capacity ten or more times of its own mass can be optimally used for the superabsorbent polymer particles. The article 1 includes a plurality of absorbing regions 6 in which the upper layer 2 and the lower layer 3 are spaced apart from each other and the superabsorbent polymer particles 4 are bonded to the lower layer 3, and a sealing region 7 in which the upper layer 2 and the lower layer 3 are joined to each other. As used herein, by "the lower layer 3 is water-permeable" is meant that the lower layer 3 allows water to permeate as easily as the upper layer 2 does. As used herein, by "the lower layer 3 is low-water-permeable" is meant that the lower layer 3 does not allow water to permeate as the upper layer 2 does. As used herein, by "the lower layer 3 is water-impermeable" is meant that the lower layer 3 is substantially water-impermeable compared to the upper layer 2. The water-permeable or low-water-permeable or water-impermeable lower layer 3 may be selectively used depending on given conditions including intended end-usages, manners of usage and manufacturing methods. In FIG. 2, a diameter of each superabsorbent polymer particle 4 is exaggeratingly indicated to distinctify the presence of these superabsorbent polymer particles 4.

The absorbing regions 6 are respectively surrounded by the sealing region 7 and contain herein the superabsorbent polymer particles 4 functioning as water absorbent material, thereby defining water-absorbing regions. In other words, the absorbing regions 6 respectively define existence regions of the superabsorbent polymer particles at a required mass per unit area. In these absorbing regions 6, the superabsorbent polymer particles 4 with a mass per unit area of 30 to 300 $g/m^2$, more preferably with a mass per unit area of 40 to 280 $g/m^2$ are uniformly bonded to the lower layer 3 overall with a hot melt adhesive 11 for fixation of the superabsorbent polymer particles. In this regard, the absorbing regions 6 may additionally contain therein a certain amount of the superabsorbent polymer particles not fixed to the lower layer 3 and an upper limit of total amount of the superabsorbent polymer particles which may be contained between the lower layer 3 and the upper layer 2 is 400 $g/m^2$. While the lower layer 3 and the upper layer 2 are preferably not joined to each other in the absorbing regions, it is difficult in a manufacturing process of the article 1 (See FIGS. 3 and 4) to avoid a situation that the upper layer 2 is unintentionally joined to the lower layer 3 over a negligibly small area.

On the assumption that the superabsorbent polymer particles 4 contained within the absorbing regions 6 are not fixed with the hot melt adhesive 11 for fixation of the superabsorbent polymer particles so as to be freely movable within the absorbing region 6, the sealing region 7 will be the region functioning to prevent these superabsorbent polymer particles 4 from getting out of this region, namely, the region serving to seal the peripheries of the absorbing regions 6. More specifically, this sealing region 6 is a non-water-absorbing region containing substantially no water-absorbent material except the upper layer 2, if it is formed of water-absorbent material, and the superabsorbent polymer particles with a mass per unit area of 20 $g/m^2$ or less having unintentionally moved into the sealing region 6 during the manufacturing process. According to the present invention, such region is referred to as a non-existence region of a required mass of the superabsorbent polymer particles per unit area. More specifically, even if this region 7 contains therein the superabsorbent polymer particles 4, such region is defined to be the sealing region so long as the mass ($g/m^2$) of the superabsorbent polymer particles 4 contained in the sealing region 7 is further less than the mass ($g/m^2$) contained in the absorbing regions 6 both on the basis of the mass per unit area of the lower layer 3. In this sealing region 7, the upper layer 2 and the lower layer 3 are joined to each other with the hot melt adhesive for sealing. The upper layer 2 and the lower layer 3 may be further welded to each other to improve a peel strength of these two layers 2, 3. In either case, the upper layer 2 and the lower layer 3 are treated so that these two layers 2, 3 are never peeled off from each other. In the article 1 exemplified in FIG. 2, the hot melt adhesive for fixation of the superabsorbent polymer particles and second hot melt adhesive 102 (See FIGS. 3 and 4) described in more detail later applied so as to overlap with each other in the sealing region 7, thereby forming the hot melt adhesive 12 for sealing with which the upper layer 2 and the lower layer 3 are joined to each other in the sealing region 7. As these hot melt adhesives, those widely used in the relevant articles may be selectively used.

The exemplified article 1 is configured to be relatively long in the longitudinal direction A. Eight segmented absorbing regions 6, namely, water-absorbing regions designated by reference numerals 6a-6h are arranged in the longitudinal direction A of the article 1. The respective absorbing regions 6a-6h have peripheries 61 defining configurations of the respective absorbing regions. The peripheries 61 in each pair of the absorbing regions 6 being adjacent in the longitudinal direction A include side edges 62 opposite to each other in the longitudinal direction A and extending in the transverse direction B. For example, referring to FIG. 1, the peripheries 61 of the absorbing regions 6a, 6b being adjacent to each other include opposite side edges 62 designated by reference numerals 62a, 62b which are opposite to each other in the longitudinal direction A and extending in the transverse direction B.

In this article 1, the sealing region 7 has opposite lateral portions 7a extending in the longitudinal direction A along opposite lateral portions of the article 1, opposite end portions 7b extending in the transverse direction B along opposite ends of the article 1 and intermediate portions 7c defined between respective pairs of the absorbing regions 6 being adjacent in the longitudinal direction A and extending in the transverse direction B. The respective intermediate portions 7c have a width W corresponding to a dimension in the longitudinal direction A which is substantially uniform.

When such article 1 is used, for example, as an absorbent structure in a disposable diaper or as a urine absorbent pad for incontinent patients, the longitudinal direction A of the article 1 and a longitudinal direction of the diaper or the pad is brought in line so the a midsection in the longitudinal direction A of the article may be positioned in the wearer's crotch region. The upper layer 2 is formed of a water-permeable sheet member and adapted to face the wearer's skin.

With use of the article 1, various advantageous effects may be provided to the diaper. For example, it is ensured that the amount of urine excreted by the wearer permeates the upper layer 2 of the respective absorbing regions 6 and then is reliably absorbed by the superabsorbent polymer particles 4 without flowing. In addition, the superabsorbent polymer particles 4 are fixed to the lower layer 3 formed of the low-water-permeable or water-impermeable sheet in this diaper so that a distribution state of the superabsorbent polymer particles 4 in the wearer's crotch region may stay constant even if the wearer's posture changes in a wide range. For this reason, the superabsorbent polymer particles 4 should not be unevenly distributed within the respective absorbing regions 6. In this way, the article 1 enables the urine to permeate the upper layer 2 over a wide area thereof and enables the absorbing regions 6 to absorb the urine over a wide area thereof. Also, the distribution state of the superabsorbent polymer particles 4 within the respective absorbing regions 6 should not be unevenly distributed to result in unevenness of the article thickness and the article 1 might locally irritate the wearer's skin. In the absorbing regions 6, the hot melt adhesive 11 for fixation of the superabsorbent polymer particles is applied to the lower layer 3 but not to the upper layer 2. In consequence, the hot melt adhesive 11 for fixation of the superabsorbent polymer particles should not interfere with the water-permeability of the upper layer 2. The superabsorbent polymer particles 4 fixed to the lower layer 3 prevent the upper layer 2 from getting closer and being eventually joined to the lower layer 3. Accordingly, the superabsorbent polymer particles 4 prevents a desired flexibility of the article 1 from being deteriorated due to a situation that the upper layer 2 is joined to the lower layer 3. In the article 1 arranged in the crotch region of the diaper, a plurality of the intermediate portions 7c extending in parallel to each other as in the exemplified article functions to facilitate the article 1 to be curved in the longitudinal direction A of the article 1. A width dimension W of the respective intermediate portions 7c functioning in this manner is preferably in a range of 2 to 15 mm.

In an example of the article 1 used for the diaper in this manner, as material of the upper layer 2, a water-permeable nonwoven fabric sheet formed of thermoplastic synthetic fibers and hydrophilized, for example, a hydrophilized SMS nonwoven fabric (spunbonded-meltblown-spunbonded) formed of polypropylene fibers may be used. One example of such an SMS nonwoven fabric is a sheet material having a mass per unit area in a range of 10 to 12 $g/m^2$ composed of a pair of spunbonded nonwoven fabrics each having a mass per unit area in a range of 4 to 5 $g/m^2$ and a meltblown nonwoven fabric having a mass per unit area in a range of 0.5 to 2 $g/m^2$ interposed between the pair of spun bonded nonwoven fabrics.

As the lower layer 3, a low-water-permeable or water-impermeable nonwoven fabric formed of hydrophobic thermoplastic synthetic fibers may be used. For example, there is a low-water-permeable SMS nonwoven fabric adapted for this purpose composed of a meltblown nonwoven fabric having a mass per unit area in a range of 0.5 to 2 $g/m^2$ interposed between two spunbonded nonwoven fabrics each formed of polypropylene fibers and having a mass per unit area in a range of 4 to 6 $g/m^2$ so as to have a mass per unit area in a range of 10 to 13 $g/m^2$ as a whole. As the lower layer 3, it is also possible to use a water-impermeable sheet formed of a plastic film having a thickness in a range of 0.01 to 0.03 mm such as a polyethylene film or a water-impermeable sheet formed of a laminate of a water-impermeable plastic film and a water-permeable or low-water-permeable nonwoven fabric. Preferably, such laminate is arranged so that the nonwoven fabric extends on the inner side of the article 1 and the water-impermeable plastic film extends on the outer side of the article 1 wherein the superabsorbent polymer particles 4 are bonded to the nonwoven fabric and the plastic film prevents body exudates from leaking out through the fiber interstices of the nonwoven fabric.

Water absorption speed of the superabsorbent polymer particles 4 depends on types of the polymer and the superabsorbent polymer particles 4 having a uniform water absorption speed may be solely used or a mixture of the superabsorbent polymer particles 4 having different water absorption speeds may be used. As an example, the superabsorbent polymer particles 4 having a water absorption speed of about 30 seconds measured by VORTEX method under the provisions of JIS K 7224 may be used with an upper limit of 400 g/m$^2$. Used amount of the superabsorbent polymer particles 4 is preferably adjusted depending on sizes of the absorbing regions 6 and manners in which the article 1 is used. In addition, as the superabsorbent polymer particles 4, those which generate eluted substances from urine as small as possible is preferably used. This is because, during contact of the superabsorbent polymer particles 4 with urine, these substances eluted from urine increase a viscosity of the urine and, in consequence, may correspondingly create a discomfort feeling against the wearer when urine comes in contact with the wearer's skin.

While the hot melt adhesive 11 for fixation of the superabsorbent polymer particles is normally applied to the lower layer 3 in the absorbing regions 6 in order to fix the superabsorbent polymer particles 4 to the lower layer 3, this hot melt adhesive 11 is sometimes applied also to the lower layer 3 in the sealing region 7. For example, referring to FIG. 2, the hot melt adhesive 11 for fixation of the superabsorbent polymer particles is applied to an upper surface 3a of the lower layer 3 so as to be distributed on its overall area with a mass per unit area in a range of 1 to 12 g/m$^2$. An amount of the hot melt adhesive 11 for fixation of the superabsorbent polymer particles per unit area is preferably reduced as far as possible to prevent the respective surfaces of the superabsorbent polymer particles 4 from being coated with the hot melt adhesive 11. The hot melt adhesive 11 for fixation of the superabsorbent polymer particles may be continually applied, for example, in a dotted-pattern or a beads-pattern or continuously applied so as to cover the overall absorbing regions 6. In any of these cases, preferably portions of the respective surfaces of the superabsorbent polymer particles 4 facing the upper surface 3a of the lower layer 3 are coated with the hot melt adhesive 11 for fixation of the superabsorbent polymer particles and bonded to the upper surface 3a but portions facing a lower surface 2b (See FIG. 2) of the upper layer 2 are not coated with the hot melt adhesive 11 for fixation of the superabsorbent polymer particles so that these portions can quickly absorb the excreted urine.

The hot melt adhesive 12 for sealing is composed of certain amount of the hot melt adhesive 11 for fixation of the superabsorbent polymer particles applied to the lower layer 3 in the sealing region 7 and second hot melt adhesive 102 to be described later with reference to FIG. 4 additionally applied with a mass per unit area in a range of 5 to 30 g/m$^2$. The respective amounts of the hot melt adhesive to be applied to the absorbing regions 6 and the sealing region 7 may be adjusted in this manner to avoid an undesirable situation such that, in the absorbing regions 6, the surfaces of the respective superabsorbent polymer particles 4 are extensively coated with the hot melt adhesive 11 for fixation of the superabsorbent polymer particles and, in consequence, the water absorption capacity as well as the water absorption speed of the superabsorbent polymer particles 4 is adversely affected and, in the sealing region 7, peeling off between the upper layer 2 and the lower layer 3 can not be reliably prevented with use of the hot melt adhesive 11 for fixation of the superabsorbent polymer particles alone. On the assumption that a partial amount of the superabsorbent polymer particles 4 is not fixed to the lower layer 3 and movably contained within the absorbing regions 6, the sealing region 7 is preferably coated with the hot melt adhesive 12 for sealing continuously or almost continuously along the peripheries of the absorbing regions 6 with which the upper layer 2 and the lower layer 3 are joined to each other, thereby preventing the superabsorbent polymer particles 4 movably contained in the absorbing regions 6 from moving from the absorbing regions 6 to the sealing region 7. As the hot melt adhesive 11 for fixation of the superabsorbent polymer particles and the hot melt adhesive 12 for sealing, the same kind of hot melt adhesive or different kinds of hot melt adhesive which firmly adhere to each other may be used. If only the adhesive 11 for fixation of the superabsorbent polymer particles applied to the sealing region 7 fulfills the function of the hot melt adhesive 12 for sealing, use of the second hot melt adhesive 102 illustrated in FIG. 4 will be unnecessary. In this case, the applied amount of the hot melt adhesive 11 for fixation of the superabsorbent polymer particles per unit area may be uniform in both the absorbing regions 6 and the sealing region 7.

While it is possible to use a plastic film instead of the nonwoven fabric as material of the lower layer 3, use of the plastic film may sometimes require increasing a quantity for application of the hot melt adhesive 11 for fixation of the superabsorbent polymer particles to bond the superabsorbent polymer particles 4 to the plastic film. In consequence, the surfaces of the superabsorbent polymer particles 4 are apt to be coated with the hot melt adhesive 11 for fixation of the superabsorbent polymer particles over an undesirably wide range.

Length dimensions in the longitudinal direction A and the transverse direction B of the absorbing region 6 in the article 1 when it is used in the diaper, more specifically, these length dimensions in the longitudinal direction A and the transverse direction B of each cell of the absorbing region 6 illustrated in FIG. 1 may be appropriately selected depending on sizes of the diaper. For example, these length dimensions in the respective directions may be set to a range of 25 to 100 mm and a range of 150 to 250 mm, respectively, and, when the length dimensions in the respective directions are set in this manner, the number of the cells of the absorbing region 6 is preferably in a range of 5 to 15. The respective lateral portions 7a and the end portions 7b of the sealing region 7 preferably have a width in a range of 5 to 30 mm.

Figure 3:
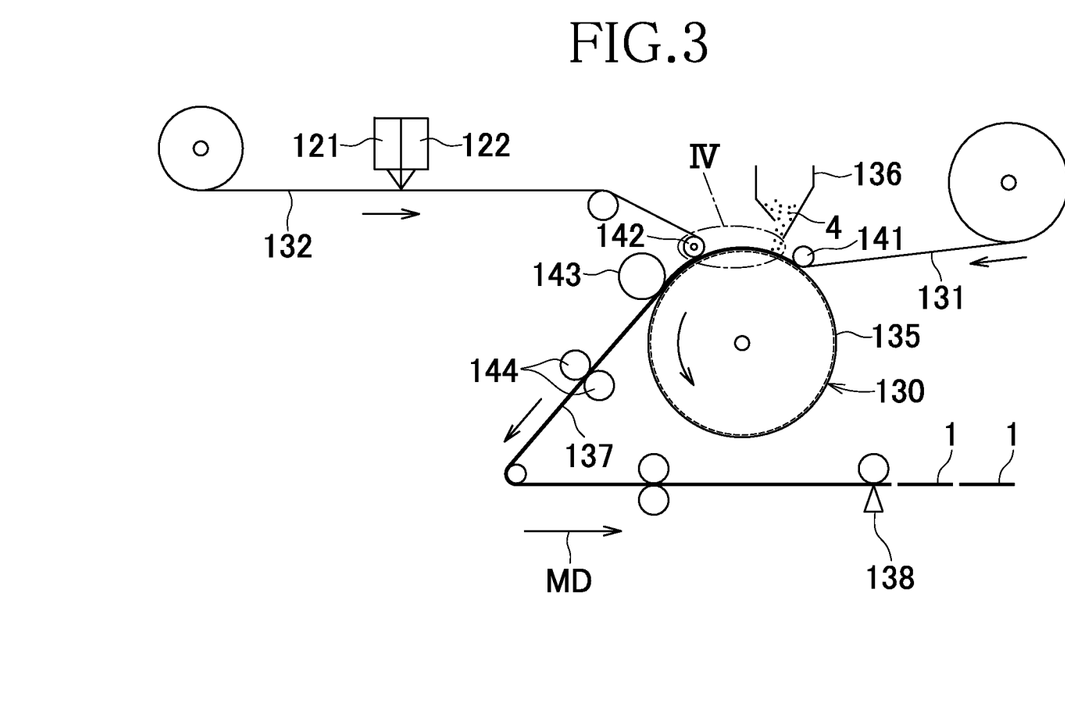
FIG. 3 is a diagram exemplifying a process of manufacturing the absorbent article.
Figure 4:
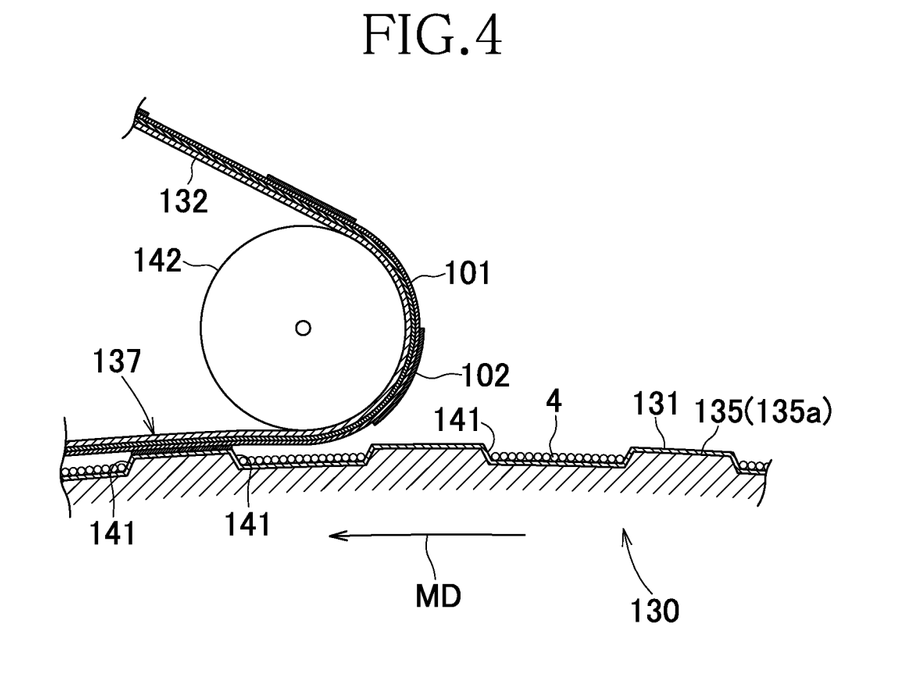
FIG. 4 is a partially scale-enlarged diagram of FIG. 3.

FIG. 3 is a diagram exemplifying a process of continuously manufacturing the articles 1 and FIG. 4 is a partially scale-enlarged diagram illustrating a suction drum 130 used in this process. Referring to FIG. 3, a first web 131 corresponding to continuous material of the upper layer 2 is supplied from the right side as viewed in FIG. 3 toward a peripheral surface 135 of the suction drum 130. The first web 131 kept in close contact with the peripheral surface 131 under a pressing effect of a guide roll 141 and a suction effect of the suction drum 130 directed toward the inside thereof is supplied with the superabsorbent polymer particles 4 from a polymer particle supplier 136 located above the suction drum 130. From the left side as viewed in FIG. 3, a second web 132 corresponding to continuous material of the lower layer 3 is continuously supplied via a guide roll 142 to the peripheral surface 135 of the suction drum 130. One surface of the second web 132 is coated by a first coater 121 located upstream of the suction drum 130 with first hot melt adhesive 101. Then, the first hot melt adhesive 101 already having been applied to the one surface of the second web 132 is partially coated by a second coater 122 located downstream of the first coater 121 with second hot melt adhesive 102. The first web 131 having been supplied with the superabsorbent polymer particles 4 and the second web 132 having been coated with the first hot melt adhesive 101 and the second hot melt adhesive 102 now join together on the peripheral surface 135 of the suction drum 130 and are joined together with the first hot melt adhesive 101 and the second hot melt adhesive 102 to form a composite web 137. The composite web 137 is cut by a cutter 138 at a certain length to provide the individual articles 1. While the first hot melt adhesive 101 corresponds, in principle, to the hot melt adhesive 11 for fixation of the superabsorbent polymer particles in the article 1, the first hot melt adhesive 101 coated to overlap the second hot melt adhesive 102 is integrated with the second hot melt adhesive 102 to form the hot melt adhesive 12 for sealing in the article 1. Details of the process of forming the composite web 137 will be described hereunder with reference to FIG. 4.

FIG. 4 illustrates a manner in which the first web 131 and the second web 132 join together on the peripheral surface 135 of the suction drum 130 illustrated herein in its sectional view. The peripheral surface 135 of the suction drum 130 is formed with a plurality of depressed portions 141 arranged in a circumferential direction. The respective depressed portions 141 have a configuration corresponding to that of the respective cells of the absorbing region 6 arranged in the longitudinal direction A in FIG. 1. Depth dimension of the depressed portion 141 is set so that the depressed portion 141 may be substantially filled with a dose of the superabsorbent polymer particles 4 supplied to the respective depressed portions 141. In the depressed portion 141, the first web 131 placed on the peripheral surface 135 is deformed along the shape of the depressed portion 141 under the suction effect of the suction drum 130 directed toward the inside thereof. The superabsorbent polymer particles 4 supplied from the polymer particle supplier 136 toward the depressed portion 141 are collected in the deformed portion of the first web 131. On a portion 135a of the peripheral surface in the form of a protruding portion defined between each pair of the adjacent depressed portions 141, 141, the first web 131 and the second web 132 join together. Then, these two webs 131, 132 are pressed between the portion 135a of the peripheral surface and a first press roll 143 and joined to each other to form the composite web 137 as these two webs 131, 132 move past the first press roll 143. The composite web 137 runs in a machine direction MD away from the suction drum 130 and now passes through a pair of second press rolls 144 wherein the superabsorbent polymer particles 4 and the first hot melt adhesive 101 are surely put in close contact with each other under the effect of these paired press rolls 144, and the superabsorbent polymer particles 4 are fixed to the second web 132 with the first hot melt adhesive 101. In this regard, while the composite web 137 is illustrated in FIG. 3 to pass through the paired second press rolls 144 obliquely with respect to the machine direction MD indicated by a horizontal arrow, the composite web 137 having left the suction drum 130 preferably approaches the paired second press rolls 144 in substantially horizontal posture so that the superabsorbent polymer particles 4 may spread rather horizontally between the first web 131 and the second web 132.

In the article 1 formed in this manner, while the first hot melt adhesive 101 may be continually applied to the absorbing region 6 and the sealing region 7, respectively, so that the first hot melt adhesive 101 may be evenly distributed in the longitudinal direction A as well as in the transverse direction B, it is also possible to coat these regions 6, 7 with the first hot melt adhesive 101 in a continuous pattern at least in one of the longitudinal direction A and the transverse direction B. For this reason, model selection for the first coater 121 used to apply the first hot melt adhesive 101 is not specified and this is true with respect to the second hot melt adhesive 102. In this regard, preferably, the hot melt adhesive 11 for fixation of the superabsorbent polymer particles in the absorbing region 6 and the hot melt adhesive 12 for sealing are continuous to one another or sufficiently adjacent to one another to ensure that a distance between these hot melt adhesives 11, 12 is restricted to 5 mm or less. Application of the hot melt adhesive 11 for fixation of the superabsorbent polymer particles in such a manner allows the hot melt adhesive 11 to spread into every corner of the absorbing region 6, thereby allowing the superabsorbent polymer particles 4 also to spread into every corner of the absorbing region 6. For example, the superabsorbent polymer particles 4 may be distributed along the opposite side edges 62 of the absorbing region 6 immediately inside the opposite side edges 62. In the absorbing region 6, the superabsorbent polymer particles 4 are preferably distributed so as to cover substantially overall the upper surface 3a (See FIG. 2) of the lower layer 3 and the superabsorbent polymer particles 4 distributed in such a manner can prevent, in the absorbing region 6, the upper layer 2 and the lower layer 3 from being joined to each other by the intermediary of the hot melt adhesive 11 for fixation of the superabsorbent polymer particles.

While, in the article 1, a total amount of the superabsorbent polymer particles 4 in the absorbing region 6 is preferably bonded and fixed to the upper surface 3a of the lower layer 3, it is also possible to implement the present invention in such a manner that the absorbing region 6 contains therein, in addition to the superabsorbent polymer particles 4 fixed to the lower layer 3, a certain amount of the superabsorbent polymer particles 4 which is not fixed to the lower layer 3 and therefore movable within the absorbing region 6. In order that the absorbing region 6 can contain therein the superabsorbent polymer particles 4 in movable condition, assuming that both the upper layer 2 and the lower layer 3 are formed of nonwoven fabrics, these nonwoven fabrics are preferably selected from the types adapted to prevent the superabsorbent polymer particles 4 from readily breaking into fiber interstices of the nonwoven fabrics or from easily passing through the fiber interstices. From such viewpoint, to be used as the upper layer 2 and the lower layer 3, respectively, preferably selected are the nonwoven fabrics which should not allow the superabsorbent polymer particles 4 to flow into the fiber interstices even when the nonwoven fabrics with the superabsorbent polymer particles 4 diffused thereon are vibrated. For implementation of the present invention, a configuration of the article 1, a configuration of the absorbing region 6 and the number of the cells forming the absorbing region 6 are not specified in particular and these shapes and the number in the exemplified embodiment may be appropriately varied. For example, it is possible to vary the configuration of the sealing region 7 so that the absorbing region 6 of the article 1 illustrated in FIG. 1 may be divided into two or three cells.

In the article 1, the absorbing region 6 may contain a mixture of the superabsorbent polymer particles 4 and second superabsorbent polymer particles (not shown) having a water absorption speed different from that of superabsorbent polymer particles 4. For example, it is possible to use the superabsorbent polymer particles having a water absorption speed $AS_1$ of 3 seconds measured by VORTEX method as the superabsorbent polymer particles 4 fixed to the lower layer 3 and to use the superabsorbent polymer particles having a water absorption speed $AS_2$ of 30 seconds measured by VORTEX method as the second superabsorbent polymer particles so that the second superabsorbent polymer particles may be bonded to the upper layer 2 in the absorbing region 6 with a second hot melt adhesive for fixation of the superabsorbent polymer particles (not shown) or bonded neither to the upper layer 2 nor to the lower layer 3, namely, mixed with the fixed first superabsorbent polymer particles 4 in a fashion freely movable within the absorbing region 6. When the article 1 including the superabsorbent polymer particles 4 having a relatively high water absorption speed $AS_1$ distributed in the vicinity of the lower layer 3 and the second superabsorbent polymer particles having a relatively low water absorption speed $AS_2$ distributed in the vicinity of the upper layer 2 is used so that the upper layer 2 may be put in contact with the wearer's skin, most part of urine excreted in early phase after the diaper has been put on the wearer's body can be absorbed by the superabsorbent polymer particles 4 laid at a large distance from the wearer's skin to shut the urine away from the diaper wearer's skin before the second superabsorbent polymer particles absorb the urine to form gel block and urine excreted later may be absorbed by the second superabsorbent polymer particles laid in the vicinity of the wearer's skin. In this way, it is possible to prevent the urine in early phase after the diaper has been put on the wearer's body from causing the wearer to experience a discomfort feeling of wetness. A total amount of the superabsorbent polymer particles 4 and the second superabsorbent polymer particles contained within the absorbing region 6 is preferably 400 g/m² or less.

The article 1 according to the present invention has the intended end-usage is not limited to the disposable diaper but may be used, for example, as a urine-absorbent pad used in combination with a diaper or a diaper cover or as a urine-absorbent pad used in combination with pants for incontinent patient. In addition, the article 1 maybe used for other absorbent articles, for example, as wipes used for water absorption treatment. In the article 1 used as wipes, a water-permeable sheet, low-water-permeable or water-impermeable sheet may be used as the lower layer 3.

REFERENCE SIGNS LIST 1 absorbent article
2 first layer
3 second layer
4 superabsorbent polymer particles
6 absorbing region (existence region of required mass per unit area of superabsorbent polymer particles)
7 sealing region (non-existence region of required mass per unit area of superabsorbent polymer particles)
11 hot melt adhesive for fixation of the superabsorbent polymer particles
12 hot melt adhesive for sealing

The invention claimed is:

1. An absorbent article having a pad configuration, the article comprising:
   a first layer, a second layer, superabsorbent polymer particles interposed between the first and second layers of which at least one is water-permeable,
wherein
   at least one of opposed surfaces of the first and second layers in the article is formed with absorbing regions coated with a hot melt adhesive for fixation of the superabsorbent polymer particles, and a sealing region coated with a hot melt adhesive for sealing and surrounding the absorbing regions,
   each of the absorbing regions defines an existence region in which a required mass per unit area of the superabsorbent polymer particles bonded to the at least one of the opposed surfaces of the first and second layers with the hot melt adhesive for fixation of the superabsorbent polymer particles exists,
   the sealing region defines a non-existence region in which the opposed surfaces of the first and second layers are joined to each other with the hot melt adhesive for sealing, and an amount of the superabsorbent polymer particles corresponding to the required mass per unit area of the superabsorbent polymer particles in the absorbing region does not exist,
   the superabsorbent polymer particles have a water-absorption speed $AS_1$ and, between the opposed surfaces of the first and second layers, second superabsorbent polymer particles having a water-absorption speed $AS_2$ lower than the water-absorption speed $AS_1$ are included between the opposed surfaces of the first and second layers defining the absorbing regions, and
   the second superabsorbent polymer particles are bonded to a remainder of the opposed surfaces of the first and second layers with a second hot melt adhesive for fixation of the second superabsorbent polymer particles.

2. The article according to claim 1, wherein, in the existence region in which the required mass per unit area of the superabsorbent polymer particles exists, the superabsorbent polymer particles are fixed thereto with a mass per unit area in a range of 30 to 300 g/m².

3. The article according to claim 1, wherein an amount of the hot melt adhesive for sealing applied to the at least one of the opposed surfaces of the first and second layers per unit area is equal to an amount of the hot melt adhesive for fixation of the superabsorbent polymer particles applied to the at least one of the opposed surfaces of the first and second layers per unit area.

4. The article according to claim 1, wherein an amount of the hot melt adhesive for sealing applied to the at least one of the opposed surfaces of the first and second layers per unit area is larger than an amount of the hot melt adhesive for fixation of the superabsorbent polymer particles applied to the one of the opposed surfaces of the first and second layers per unit area.

5. The article according to claim 1, wherein the first and second layers are water-permeable.

6. The article according to claim 5, wherein the first and second layers being water-permeable are formed of hydrophilic nonwoven fabrics of thermoplastic synthetic fibers.

7. The article according to claim 1, wherein
   one of the first and second layers is formed of a water-permeable sheet and a remainder of the first and second layers is formed of a water-impermeable or low-water-permeable sheet, and
   the superabsorbent polymer particles are bonded to the water-impermeable or low-water-permeable sheet.

8. The article according to claim 7, wherein
   the water-impermeable or low-water-permeable sheet is a hydrophobic nonwoven fabric of thermoplastic synthetic fibers or a laminate composed of the hydrophobic nonwoven fabric and a water-impermeable plastic film, and
   the superabsorbent polymer particles are bonded to the hydrophobic nonwoven fabric.

9. The article according to claim 1, wherein the hot melt adhesive for fixation of the superabsorbent polymer particles in the absorbing regions and the hot melt adhesive for sealing in the sealing region are continuous to one another.

10. The article according to claim 1, wherein the hot melt adhesive for fixation of the superabsorbent polymer particles in the absorbing regions and the hot melt adhesive for sealing in the sealing region are adjacent to one another.

11. The article according to claim 1, wherein the hot melt adhesive for fixation of the superabsorbent polymer particles and the hot melt adhesive for sealing are the same adhesive.

12. An absorbent article having a pad configuration, the article comprising:
- a first layer, a second layer, superabsorbent polymer particles interposed between the first and second layers of which at least one is water-permeable, wherein
- at least one of opposed surfaces of the first and second layers in the article is formed with absorbing regions coated with a hot melt adhesive for fixation of the superabsorbent polymer particles, and a sealing region coated with a hot melt adhesive for sealing and surrounding the absorbing regions,
- each of the absorbing regions defines an existence region in which a required mass per unit area of the superabsorbent polymer particles bonded to the at least one of the opposed surfaces of the first and second layers with the hot melt adhesive for fixation of the superabsorbent polymer particles exists,
- the sealing region defines a non-existence region in which the opposed surfaces of the first and second layers are joined to each other with the hot melt adhesive for sealing, and an amount of the superabsorbent polymer particles corresponding to the required mass per unit area of the superabsorbent polymer particles in the absorbing region does not exist,
- the superabsorbent polymer particles have a water-absorption speed $AS_1$ and, between the opposed surfaces of the first and second layers, second superabsorbent polymer particles having a water-absorption speed $AS_2$ lower than the water-absorption speed $AS_1$ are included between the opposed surfaces of the first and second layers defining the absorbing regions, and
- wherein the second superabsorbent polymer particles are movable between the opposed surfaces of the first and second layers.

* * * * *